(12) United States Patent
Doi

(10) Patent No.: US 6,368,616 B1
(45) Date of Patent: Apr. 9, 2002

(54) AQUEOUS SUSPENSION FOR NASAL ADMINISTRATION OF LOTEPREDNOL

(75) Inventor: Koji Doi, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/341,522

(22) PCT Filed: Jan. 14, 1998

(86) PCT No.: PCT/JP98/00108

§ 371 Date: Jul. 13, 1999

§ 102(e) Date: Jul. 13, 1999

(87) PCT Pub. No.: WO98/31343

PCT Pub. Date: Jul. 23, 1998

(30) Foreign Application Priority Data

Jan. 16, 1997 (JP) ............................................. 9-019664

(51) Int. Cl.$^7$ ................................................. A61F 13/00
(52) U.S. Cl. ....................................... 424/434; 514/781
(58) Field of Search ........................... 424/434; 514/781

(56) References Cited

U.S. PATENT DOCUMENTS 5,916,550 A    6/1999  Inada et al. .............. 424/78.04

FOREIGN PATENT DOCUMENTS

| EP | 0709099 | 5/1996 |
| WO | 95/11669 | 5/1995 |
| WO | WO 9511669 | 5/1995 |

*Primary Examiner*—Carlos A. Azpuru
(74) *Attorney, Agent, or Firm*—Wenderoth, Lind & Ponack, L.L.P.

(57) ABSTRACT

An aqueous suspension for nasal administration which contains loteprednol etabonate and microcrystalline cellulose carmellose sodium. This aqueous suspension can be administered to nasal mucosa to treat inflammation or allergy.

5 Claims, No Drawings

AQUEOUS SUSPENSION FOR NASAL ADMINISTRATION OF LOTEPREDNOL

This application is a 371 application of International Application No. PCT/JP98/00108 filed Jan. 14, 1998, which is ased on Japanese Priority Application No. 9-019664 filed Jan. 16, 1997.

1. Field of the Invention

The present invention relates to a stabilized aqueous suspension of loteprednol etabonate having antiinflammatory and antialletgic activities for use as nasal drops.

2. Background of the Invention

Loteprednol etabonate is a synthetic adrenocortical hormone having excellent antiinflammatory and antiallergic activities, and because of those activities coupled with a low dermal (mucosal) irritation potential and a low risk for side effects, this compound is expected to be of value as a drug for external application, e.g. an ointment or a liquid.

However, since loteprednol etabonate is substantially insoluble in water, it has to be provided in the form of a suspension as far as a liquid dosage form for external application is concerned. Heretofore, as a suspending agent-stabilizer for such a water-insoluble (inclusive of hardly water-soluble) drug, methylcellulose (MC), hydroxypropylmethylcellulose (HPMC), carboxymethylcellulose sodium (CMC-Na), or polyvinylpyrrolidone (PVP), for instance, has been generally employed. As far as loteprednol etabonate is concerned, however, none of said MC, HPMC, CMC-Na, and PVP in its usual formulating amount is capable of providing sufficiently stabilized suspensions. Thus, if such a suspension is allowed to stand for a long time, e.g. 3 months or longer, particles of loteprednol etabonate undergo aggregation and precipitation to form deposits on the container bottom and side walls and once this occurs, the original condition immediately after preparation cannot be reestablished even if the container is shaken or swirled vigorously. Of course, the concentration of the active ingredient in the suspension will be deviating from the concentration immediately after preparation. Furthermore, when the dosage form is nasal drops, the suspension is provided in the conventional nasal sprayer but the aggregation and deposition of particles take place in the nozzle part of the quantitative delivery pump to cause a failure to deliver the designed quantity or clogging of the nozzle orifices.

Therefore, how an aqueous suspension of loteprednol etabonate could be kept stable over a long time has been an important question to be answered.

From the above viewpoint, a stable aqueous suspension of loteprednol etabonate has been proposed by WO 95/11669. However, when the suspension is administered to a nasal cavity, it runs down from the nasal foramen because of its low viscosity less than 80 centipoise. Therefore, the suspension has drawbacks that its retention time is too short to achieve pharmaceutical effect and that the feeling-of-use is not good.

SUMMARY OF THE INVENTION

The inventor of the present invention explored the possibility of stabilizing an aqueous suspension of loteprednol etabonate and of improving intranasal retention of the active ingredients and the feeling-of-use using thickeners including cellulose derivatives such as methylcellulose, carboxymethylcellulose sodium, hydroxypropylmethylcellulose, etc., synthetic macromolecular compounds such as polyvinyl alcohol, polyvinylpyrrolidone, carboxyvinyl polymer, etc., and saccharides such as sorbitol, mannitol, sucrose, etc.; cationic surfactants including quaternary ammonium salts; anionic surfactants including alkylsulfates; and nonionic surfactants including polysorbate 80, polyoxyethylene hydrogenated castor oil, etc. As a result, they discovered that microcrystalline cellulose carmellose sodium is not only highly effective in stabilizing a suspension of loteprednol etabonate but also has a low dermal (mucosal) irritation potential, a favorable feeling of use, and the property to enhance the muscosal retention of the active ingredient and, based on the finding, have developed the present invention. The present invention, therefore, is directed to:

(1) an aqueous suspension for nasal administration which comprises loteprednol etabonate and microcrystalline cellulose carmellose sodium;

(2) The aqueous suspension (1), which comprises 0.05–3 w/w % of loteprednol etabonate and 0.5–10 w/w % of microcrystalline cellulose carmellose sodium;

(3) The aqueous suspension (1), which comprises 0.1–1.5 w/w % of loteprednol etabonate and 1–5 w/w % of microcrystalline cellulose carmellose sodium;

(4) A method of treating inflammation or allergy which comprises administering an effective amount of the aqueous suspension for nasal administration comprising loteprednol etabonate and microcryatalline cellulose carmellose sodium to nasal mucosa; and (5) The method according to (4), wherein the aqueous suspension for nasal administration comprises 0.05–3 w/w % of loteprednol etabonate and 0.5–10 w/w % of microcrystalline cellulose carmellose sodium.

DETAILED DESCRIPTION OF THE INVENTION

The concentration of loteprednol etabonate in the aqueous suspension for nasal administration according to the present invention is preferably 0.05–3 w/w % and more preferably 0.1–1.5 w/w %.

Meanwhile, microcrystalline cellulose carmellose sodium is generally a mixture containing not less than 80 weight % of crystalline cellulose and 9–13 weight % of carmellose sodium. Though it depends on other additives present, its concentration in the aqueous suspension is preferably 0.5–10 w/w % and more preferably 1–5 w/w %.

The aqueous suspension for nasal administration according to the present invention may contain, in addition to loteprednol etabonate, one or more other active substances such as a nonsteroidal antiinflammatory agent, e.g. mefenamic acid, an antihistaminic, e.g. clemastine fumarate, terfenadine, chlotpheniramine maleate, diphenhydramine hydrochloride, etc., an antiallergic agent such as tranilast, sodium cromoglycate, ketotifen fumarate, etc., an antibiotic, e.g. erythromycin, tetracycline, etc., and/or an antimicrobial agent, e.g. sulfamethizole, sulfamethoxazole, sulfisoxazole, etc., each in a suitable amount.

The aqueous suspension for nasal administration according to the present invention may further contain other pharmacologically active substances, such as a vasoconstrictor, a surface anesthetic, etc., in suitable amounts. The vasoconstrictor includes but is not limited to naphazoline nitrate and phenylephrine hydrochloride. The surface anesthetic includes but is not limited to lidocaine, lidocaine hydrochloride, and mepivacaine hydrochloride. These pharmacologically active substances are used in a proportion of generally 0.01–10 w/w % and preferably 0.05–5 w/w %.

The aqueous suspension for nasal administration according to the present invention may contain various additives which are broadly used in nasal drops in general. Among such additives are preservatives, isotonizing agents, buffers, stabilizers, pH control agents, and suspending agents. The preservative that can be used includes parabens (e.g. methyl p-hydroxybenzoate, propyl p-hydroxybenzoate, etc.), invert soaps (e.g. benzalkonium chloride, benzethonium chloride, chlorhexidine gluconate, cetylpyridinium chloride, etc.), alcohol derivatives (e.g. chlorobutanol, phenethyl alcohol, etc.), organic acids (e.g. dehydroacetic acid, sorbic acid, etc.), phenols (e.g. p-chloromethoxyphenol, p-chlorometacresol, etc.), and organomercury compounds (e.g. thimerosal, phenylmercury nitrate, nitromersol, etc.). The isotonizing agent includes but is not limited to glycerin, propylene glycol, sorbitol, and mannitol. The buffer that can be used includes boric acid, phosphoric acid, acetic acid, and amino acids, among others. The stabilizer includes antioxidants (e.g. dibutylhydroxytoluene (BHT), butylhydroxyanisole (BHA), propyl gallate, etc.), and chelating agents (edetic acid, citric acid, etc.). The pH control agent includes hydrochloric acid, acetic acid, sodium hydroxide, phosphoric acid, citric acid, etc. As the suspending agent, various surfactants (nonionic surfactants such as polysorbate 80, polyoxyethylene hydrogenated castor oil, tyloxapol; cationic surfactants such as quaternary ammonium salts; anionic surfactants such as alkylsulfates; and amphoteric surfactants such as lecithin) can be employed.

The addition levels of such additives vary with different active ingredients and their amounts but it is generally preferable that the physiological condition of the nose (isotonic to nasal discharge) be simulated. Typically, the osmotic pressure range should correspond to 0.2–4 w/w % saline, preferably 0.5–2 w/w % saline, and more preferably 0.9–1.5 w/w % saline.

The aqueous suspension for nasal administration according to the present invention is preferably provided in the pH range generally used for nasal drops, i.e. pH 5–7.

The aqueous suspension for nasal administration according to the present invention is provided in the osmotic pressure range used for nasal administration in general, generally 140–1140 mOsm, preferably 200–870 mOsm, and more preferably 280–310 mOsm.

The aqueous suspension for nasal administration according to the present invention is preferably provided in the viscosity ranges so as to be well retained in the nasal cavity and so as not to be dripped down from the nasal foramen after administration, in general, 400–3000 centipoise, preferably, 1000–1600 centipoise, and more preferably, 1200–1450 centipoise.

The aqueous suspension for nasal administration according to the present invention can be produced by the per se known technology. For example, it can be produced by the method described in Prescribing Guidelines IX (edited by Japanese Association of Pharmacists, 128–129, published by Yakuji Nippo, Ltd.).

The aqueous suspension for nasal administration according to the present invention can be administered by the method employed for known nasal drops in general, for example by the spray method or the drip method. Taking the spray method as an example, although it depends on the patient's age, body weight and condition, the recommended dosage and administration for the therapy of allergic rhinitis or vasomotor rhinitis in an adult patient comprise sniffing 1–2 sprays from a nasal dispenser nozzle once or twice daily. When the drip method is employed, although it depends on the patient's age, body weight, and condition, the recommended dosage and administration for the therapy of allergic rhinitis in an adult comprise dripping 2–3 drops of an aqueous suspension of the invention, which contains 0.05–3.0 w/w % or preferably 0.1–1.5 w/w % of loteprednol etabonate, into the nostril in standing or sedentary position with the neck bent back with a frequency of 1–2 times daily.

EXAMPLES

The following working and experimental examples are intended to further describe the invention and illustrate the effect of the invention. It should be understood, however, that these are merely illustrative and should by no means be construed as defining the scope of the invention.

Example 1

Recipe

| | |
|---|---|
| Loteprednol etabonate | 0.5 g |
| Concentrated glycerin | 2.6 g |
| Polysorbate 80 | 0.2 g |
| Microcrystalline cellulose carmellose sodium | 2.0 g |
| Citric acid | q.s. |
| Benzalkonium chloride | 0.005 g |
| Purified water to make | 100 g (pH 5.5) |

Procedure

With a homomixer (6000 rpm), 90 g of purified water, 0.5 g of loteprednol etabonate, 2.6 g of concentrated glycerin, 0.5 ml of 1% benzalkonium chloride solution, and 0.2 g of polysorbate 80 were stirred for 30 minutes. To this liquid mixture was added 2.0 g of microcrystalline cellulose carmellose sodium("Avicel RC-A591 NF", produced by Asahi Chemical Industry Co., Ltd.) and the whole mixture was further stirred with a mixer (750 rpm) for 60 minutes. This is followed by addition of a suitable amount of citric acid as well as purified water to bring the pH to 5.5. The mixture was further stirred for 10 minutes to provide 100 g of an aqueous suspension (a). The viscosity of the suspension measured with BL type viscometer (Number of revolution: 30 rpm, Adaptor No. 3, produced by Tokimech Co., Ltd.) was 1160 centipoise.

Example 2

Recipe

| | |
|---|---|
| Loteprednol etabonate | 0.5 g |
| Concentrated glycerin | 2.6 g |
| Polysorbate 80 | 0.2 g |
| Microcrystalline cellulose carmellose sodium | 3.0 g |
| Citric acid | q.s. |
| Benzalkonium chloride | 0.005 g |
| Purified water to make | 100 g (pH 5.5) |

By the same procedure as described in Example 1, 100 g of an aqueous suspension (b) for nasal administration was prepared. The viscosity of the suspension was 1380 centipoise.

Example 3

Recipe

| | |
|---|---|
| Loteprednol etabonate | 1.0 g |
| Concentrated glycerin | 2.6 g |
| Polysorbate 80 | 0.2 g |
| Microcrystalline cellulose carmellose sodium | 3.0 g |
| Citric acid | q.s. |
| Benzalkonium chloride | 0.005 g |
| Purified water to make | 100 g (pH 5.5) |

By the same procedure as described in Example 1, 100 g of an aqueous suspension (c) for nasal administration was prepared. The viscosity of the suspension was 1440 centipoise.

Example 4

| Recipe | |
|---|---|
| Loteprednol etabonate | 0.5 g |
| Propylene glycol | 2.0 g |
| Polyoxyethylene hydrogenated castor oil 60 | 0.2 g |
| Microcrystalline cellulose carmellose sodium | 3.0 g |
| Phosphoric acid | q.s. |
| Benzethonium chloride | 0.005 g |
| Purified water to make | 100 g (pH 5.5) |

By the same procedure as described in Example 1, 100 g of an aqueous suspension (d) for nasal administration was prepared. The viscosity of the suspension was 1340 centipoise.

Experimental Example 1
Feeling-of-use test

The aqueous suspensions (a) through (d) prepared in Examples 1 through 4 and an aqueous suspension (e) (pH 5.5) not containing microcrystalline cellulose carmellose sodium but otherwise identical with (a) were used as test drugs.

Each of the above aqueous suspensions (a)–(e) was filled in 8 ml nasal sprayers and 5 panelists were instructed to spray 70 μl of the aqueous suspension into their nostrils and evaluate the feeling of use. The results are presented in Table 1.

TABLE 1

| Suspension | Result |
|---|---|
| (a) | All of the 5 panelists reported neither drippings from the nose after application nor irritation |
| (b) | All of the 5 panelists reported neither drippings from the nose after application nor irritation |
| (c) | All of the 5 panelists reported neither drippings from the nose after application nor irritation |
| (d) | All of the 5 panelists reported neither drippings from the nose after application nor irritation |
| (e) | All of the 5 panelists reported discomfort with drippings from the nose after application. |

Experimental Example 2
Suspension Stability Test

The aqueous suspensions (a)–(e) prepared as above were respectively filled in polyethylene containers (8 ml) for nasal administration and the homogeneity of each suspension was evaluated immediately after preparation, on day 7 after preparation, and after 3 months of storage at 25° C. The results are presented in Table 2.

TABLE 2

| Suspension | Immediately after preparation | 7 days | 3 momths |
|---|---|---|---|
| (a) | No floating crystals, with the water phase being thoroughly homogeneous | No floating crystals, with the water phase being thoroughly homogeneous | No floating crystals, with the water phase being thoroughly homogeneous |
| (b) | No floating crystals, with the water phase being thoroughly homogeneous | No floating crystals, with the water phase being thoroughly homogeneous | No floating crystals, with the water phase being thoroughly homogeneous |
| (c) | No floating crystals, with the water phase being thoroughly homogeneous | No floating crystals, with the water phase being thoroughly homogeneous | No floating crystals, with the water phase being thoroughly homogeneous |
| (d) | No floating crystals, with the water phase being thoroughly homogeneous | No floating crystals, with the water phase being thoroughly homogeneous | No floating crystals, with the water phase being thoroughly homogeneous |
| (e) | Some crystals were afloat on the water phase. | Because some crystals was afloat on the water phase immediately after preparation, no further assessment was made. | Because some crystals was afloat on the water phase immediately after preparation, no further assessment was made. |

Effect of the Invention

The aqueous suspension for nasal administration according to the present invention remains stable over a long period of time, without signs of aggregation, precipitation, or deposits of the active ingredient loteprednol etabonate particles. Moreover, after being sprayed into the nostrils, the suspension is well retained on the mucosal surface and does not drip. In addition, the suspension does not elicit an irritable response, offering a very satisfactory feeling of use.

What is claimed is:

1. An aqueous suspension for nasal administration which comprises loteprednol etabonate and microcrystalline cellulose carmellose sodium.

2. The aqueous suspension for nasal administration according to claim 1, which contains 0.05–3 w/w % of loteprednol etabonate and 0.5–10 w/w % of microcrystalline cellulose carmellose sodium.

3. The aqueous suspension for nasal administration according to claim 1, which contains 0.1–1.5 w/w % of loteprednol etabonate and 1–5 w/w % of microcrystalline cellulose carmellose sodium.

4. A method of treating inflammation or allergy which comprises administering an effective amount of the aqueous suspension for nasal administration comprising loteprednol etabonate and microcryatalline cellulose carmellose sodium to nasal mucosa.

5. The method according to claim 4, wherein the aqueous suspension for nasal administration comprises 0.05–3 w/w % of loteprednol etabonate and 0.5–10 w/w % of microcrystalline cellulose carmellose sodium.

* * * * *